US011484979B2

(12) United States Patent
Brown et al.

(10) Patent No.: US 11,484,979 B2
(45) Date of Patent: Nov. 1, 2022

(54) PRECISION TRIPOD MOTION SYSTEM WITH SIX DEGREES OF FREEDOM (71) Applicant: ALIO Industries, Inc., Wheat Ridge, CO (US)

(72) Inventors: Nathan Lyons Brown, Littleton, CO (US); Clement William Hennessey, Golden, CO (US); Daniel Fording Crews, Evergreen, CO (US)

(73) Assignee: ALIO INDUSTRIES, INC., Wheat Ridge, CO (US)

( * ) Notice: Subject to any disclaimer, the term of this patent is extended or adjusted under 35 U.S.C. 154(b) by 601 days.

(21) Appl. No.: 15/633,335

(22) Filed: Jun. 26, 2017

(65) Prior Publication Data

US 2017/0291270 A1    Oct. 12, 2017

Related U.S. Application Data (63) Continuation of application No. 14/096,852, filed on Dec. 4, 2013, now Pat. No. 9,694,455.
(Continued)

(51) Int. Cl.
*B25J 17/02* (2006.01)
*B23Q 3/04* (2006.01)
(Continued)

(52) U.S. Cl.
CPC ............ *B23Q 3/04* (2013.01); *B23Q 1/4809* (2013.01); *B25J 9/0045* (2013.01);
(Continued)

(58) Field of Classification Search
CPC ............... B25J 17/0266; B25J 9/0045; B25J 17/00–17/0291; Y10T 74/20305;
(Continued)

(56) References Cited

U.S. PATENT DOCUMENTS 5,270,625 A * 12/1993 Neff ................... G05B 19/23
                                                                318/560
5,279,176 A    1/1994 Tahmasebi et al.
(Continued)

FOREIGN PATENT DOCUMENTS

| EP | 1027554 | 4/1999 |
| EP | 1637277 | 3/2006 |
| WO | 9920933 | 4/1999 |

OTHER PUBLICATIONS

IEEE Journal of Robotics and Automation, vol. 4, No. 3, Jun. 1988 (Year: 1988).*
(Continued)

*Primary Examiner* — Mahdi H Nejad (57) ABSTRACT

A precision tripod motion system is provided. The tripod motion system in one example includes a bottom plate including three spaced-apart bottom single-degree-of-freedom hinges, a top plate including three spaced-apart top three-degrees-of-freedom (TDOF) joints, wherein the top plate is configured to receive a workpiece. Each linear actuator of three linear actuators is coupled to an associated SDOF hinge of the bottom plate and coupled to an associated TDOF joint of the top plate. Each linear actuator is configured to change length over a linear actuation span and configured to return the top plate to a predetermined set position after the top plate is displaced by an external force Each linear actuator includes a ball coupled to the associated three TDOF joint and a positioning actuator configured to move the ball to the predetermined set position prior to the return of the top plate to the predetermined set position.

18 Claims, 10 Drawing Sheets

Related U.S. Application Data (60) Provisional application No. 61/733,834, filed on Dec. 5, 2012, provisional application No. 61/733,822, filed on Dec. 5, 2012.

(51) Int. Cl.
*B25J 9/00* (2006.01)
*B23Q 1/48* (2006.01)
*A61B 17/62* (2006.01)
*B23Q 1/54* (2006.01)

(52) U.S. Cl.
CPC .......... *B25J 17/0266* (2013.01); *A61B 17/62* (2013.01); *B23Q 1/5462* (2013.01); *Y10S 901/19* (2013.01); *Y10S 901/23* (2013.01); *Y10T 74/20305* (2015.01); *Y10T 74/20329* (2015.01)

(58) Field of Classification Search
CPC . Y10T 74/20329; A61B 17/62; B23Q 1/5462; B23Q 3/04; B23Q 1/4809
USPC ...... 74/490.01, 490.05, 490.07, 490.08, 201; 901/19, 27, 28
See application file for complete search history.

(56) References Cited

U.S. PATENT DOCUMENTS

| | | | |
|---|---|---|---|
| 5,376,049 A | 12/1994 | Welschof et al. | |
| 5,378,972 A | 1/1995 | Takenaka et al. | |
| 5,773,951 A * | 6/1998 | Markowski | H01L 21/681 318/625 |
| 5,901,936 A | 5/1999 | Bieg | |
| 6,047,610 A | 4/2000 | Stocco et al. | |
| 6,330,837 B1 | 12/2001 | Charles et al. | |
| 6,418,811 B1 | 7/2002 | Rosheim | |
| 6,474,915 B1 * | 11/2002 | Wildenberg | B23Q 1/5462 409/235 |
| 6,477,912 B2 | 11/2002 | Song et al. | |
| 6,497,548 B1 | 12/2002 | Roy et al. | |
| 6,602,042 B2 | 8/2003 | Roy et al. | |
| 6,648,583 B1 | 11/2003 | Roy et al. | |
| 6,671,975 B2 | 1/2004 | Hennessey | |
| 6,719,506 B2 | 4/2004 | Chang et al. | |
| 6,729,202 B2 | 5/2004 | Gosselin et al. | |
| 6,769,194 B2 | 8/2004 | Hennessey | |
| 6,808,344 B2 | 10/2004 | Chen | |
| 7,077,621 B2 * | 7/2006 | Ruden | B65G 47/901 414/749.1 |
| 7,275,332 B2 | 10/2007 | Blanding | |
| 7,707,907 B2 | 5/2010 | Bonev | |
| 7,849,762 B2 | 12/2010 | Viola | |
| 8,215,199 B2 | 7/2012 | Marcroft et al. | |
| 8,225,692 B2 | 7/2012 | Kock et al. | |
| 8,227,768 B2 | 7/2012 | Smick et al. | |
| 8,333,526 B2 | 12/2012 | Long | |
| 8,783,127 B2 | 7/2014 | Neumann | |
| 8,956,068 B2 | 2/2015 | Mekid et al. | |
| 9,694,455 B2 * | 7/2017 | Brown | B25J 9/0045 |
| 2003/0106230 A1 * | 6/2003 | Hennessey | B25J 17/0216 33/645 |
| 2007/0137476 A1 | 6/2007 | Neumann | |
| 2007/0151389 A1 | 7/2007 | Prisco et al. | |
| 2008/0011117 A1 | 1/2008 | Hennessey et al. | |
| 2008/0039973 A1 | 2/2008 | Ueno et al. | |
| 2009/0205457 A1 | 8/2009 | Neumann | |
| 2010/0096935 A1 | 4/2010 | Hennessey et al. | |
| 2010/0122602 A1 * | 5/2010 | Marcroft | B25J 17/0216 74/490.03 |
| 2010/0139436 A1 | 6/2010 | Kawashima et al. | |
| 2010/0234844 A1 | 9/2010 | Edelhauser et al. | |
| 2010/0250004 A1 | 9/2010 | Makino et al. | |
| 2011/0056074 A1 | 3/2011 | Jonas et al. | |
| 2011/0247446 A1 | 10/2011 | Namoun et al. | |
| 2011/0306473 A1 | 12/2011 | Saglia et al. | |
| 2012/0090423 A1 | 4/2012 | Helmer et al. | |
| 2012/0168593 A1 | 7/2012 | Mekid et al. | |
| 2012/0209427 A1 * | 8/2012 | Kung | B25J 9/1607 700/245 |
| 2012/0323345 A1 | 12/2012 | Jonas et al. | |
| 2013/0061710 A1 | 3/2013 | Long | |
| 2014/0033851 A1 | 2/2014 | Hermey et al. | |
| 2014/0042845 A1 | 2/2014 | Nickols | |
| 2014/0150593 A1 * | 6/2014 | Brown | B25J 9/0045 74/490.05 |
| 2014/0151947 A1 * | 6/2014 | Brown | B25J 9/0045 269/58 |
| 2014/0263883 A1 | 9/2014 | Rushworth et al. | |
| 2014/0331806 A1 | 11/2014 | Nagatsuka | |
| 2015/0114163 A1 | 4/2015 | Rosheim | |
| 2017/0291270 A1 * | 10/2017 | Brown | B25J 9/0045 |

OTHER PUBLICATIONS

IEEE Micro-Positioning of Linear-Piezoelectric Motors Based on a Learning Nonlinear PID Controller by K.K. Tan, Tong Heng Lee and Huixing X. Zhou, vol. No. 4, Dec. 2001 (Year: 2001).*

56. IEEE Transactions on Robotics and Automation, vol. 7. No. 5, Oct. 1991, A Three-Degrees-of-Freedom Micromotion In-Parallel Actuated Manipulator by Kok-Meng Lee and Shankar Arjunan (Year: 1991).*

IEEE Transactions on Robotics and Automation, vol. 7, No. 5, Oct. 1991 (A Three-Degrees-of-Freedom Micromotion In-Parallel Actuated Manipulator) (Year: 1991).*

R.H. Taylor, R.L. Hollis, M.A. Lavin, "Precise Manipulation with Endpoint Sensing", IBM J, Res. Development, vol. 29, No. 4, Jul. 1985.

"Advances in Materials Manufacturing Science and Technology XIII", vol. 1-71.5. Workspace Analysis of UPS-2RPS Parallel Mechanism. Trans Tech Publications Ltd. 2009 Online version at : http://app.knovel.com/hotlink/pdf/id:kt009IUM52/advancs-in-materials-2/works.

Products Page at Alio Website—Parallel Kinematic Robotics (Ceramic Servo Motor Tripod), Alio Industries.

CNC Machine Tools, Copyright 2009, IGI Global, pp. 185-186.

IEEE Journal of Robotics and Automation, vol. 4., No. 3, Jun. 1988. A New Parallel Kinematic Machine UPS-2RPS and Kinematics Analysis, Copyright 2009.

Parallel Kinematics Motion Systems, ALIO 6-D True Nano Precision Motion Systems.

Guo, Dongming Wang, Jun Jia, Zhenyuan Kang, Renke, Gao, Hang Wang, Xuyue (2009), Advances in Materials Manufacturing Science and Technology XIII, vol. 1-71.5 Workspace Analysis of UPS-2RPS Parallel Mechanism. Trans Tech Publications Ltd.

Xu, Yun, (2009) "Integrating Advanced Computer-Aided Design, Manufacturing, and Numerical Control: Principles and Implementations"—8.8 Parallel Machine Tools: A Little "Sidetrack", IGI Global.

Qin, Yi, (2010). Micro-Manufacturing Engineering and Technology—19.5.2 Hexapod M-850 Micro-Robot. Elsevier.

Samuel, Andrew Weir, John (2005) Introduction to Engineering Design—Modeling, Synthesis and Problem Solving Strategies—5. 4.1 Optimum Design of Tripod. Elsevier.

* cited by examiner

PRECISION TRIPOD MOTION SYSTEM WITH SIX DEGREES OF FREEDOM

CROSS-REFERENCE TO RELATED APPLICATIONS

This application is a continuation of and claims priority to U.S. patent application Ser. No. 14/096,852, entitled "Precision Tripod Motion System With Six Degrees Of Freedom", filed Dec. 4, 2014, which claims priority to U.S. Provisional Patent Application No. 61/733,822, entitled "Hybrid Parallel Kinematic Motion System", and to U.S. Provisional Patent Application Ser. No. 61/733,834, entitled "Tripod Parallel Kinematic Precision Motion System", both filed on Dec. 5, 2012, the contents of which are hereby incorporated by reference in their entirety for all purposes.

TECHNICAL BACKGROUND

Motion systems are mechanical systems that are used to hold and position a workpiece, such as in manufacturing, machining, or industrial processes, for example. Motion systems used to position a workpiece typically require a high degree of accuracy in order to achieve a highly precise positioning of the workpiece.

In order to be able to achieve a large number of working positions, a motion system may employ multiple actuator devices. The multiple actuator devices can be singly or jointly actuated in order to move and position a platform or portion holding a workpiece. Complicated actuator systems lead to additive tolerances and therefore to reduced positional accuracy. Further, complicated interactions between components can lead to poor stability within the system.

A drawback of prior art motion systems is that motion systems employing a large number of actuator devices suffer from accumulated error tolerances, resulting in complicated motion systems that cannot provide a high level of positional accuracy. Typical prior art motion systems provide micron order performance, at best, due to additive tolerance errors from six moving hardware axes. Another drawback of prior art motion systems is an inability to return to a set position when disturbed by an external force.

OVERVIEW

A precision tripod motion system is provided. The tripod motion system in one example includes a bottom plate including three spaced-apart single-degree-of-freedom (SDOF) hinge portions, a top plate including three spaced-apart top TDOF joint portions, with the top plate configured to receive a workpiece, three linear actuators pivotally coupled to the three bottom SDOF hinge portions of the bottom plate and coupled to the three top TDOF joint portions of the top plate, with each linear actuator of the three linear actuators configured to change length over a linear actuation span, and a rotator component and/or a positioning table affixed to the top plate and the bottom plate. The tripod motion system is additionally coupled to a rotator component and a positioning table to provide six degrees of freedom of motion.

This Overview is provided to introduce a selection of concepts in a simplified form that are further described below in the Technical Disclosure. It should be understood that this Overview is not intended to identify key features or essential features of the claimed subject matter, nor is it intended to be used to limit the scope of the claimed subject matter.

DETAILED DESCRIPTION

The following description and associated drawings teach the best mode of the invention. For the purpose of teaching inventive principles, some conventional aspects of the best mode may be simplified or omitted. The following claims specify the scope of the invention. Some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by claims and their equivalents.

Figure 1:
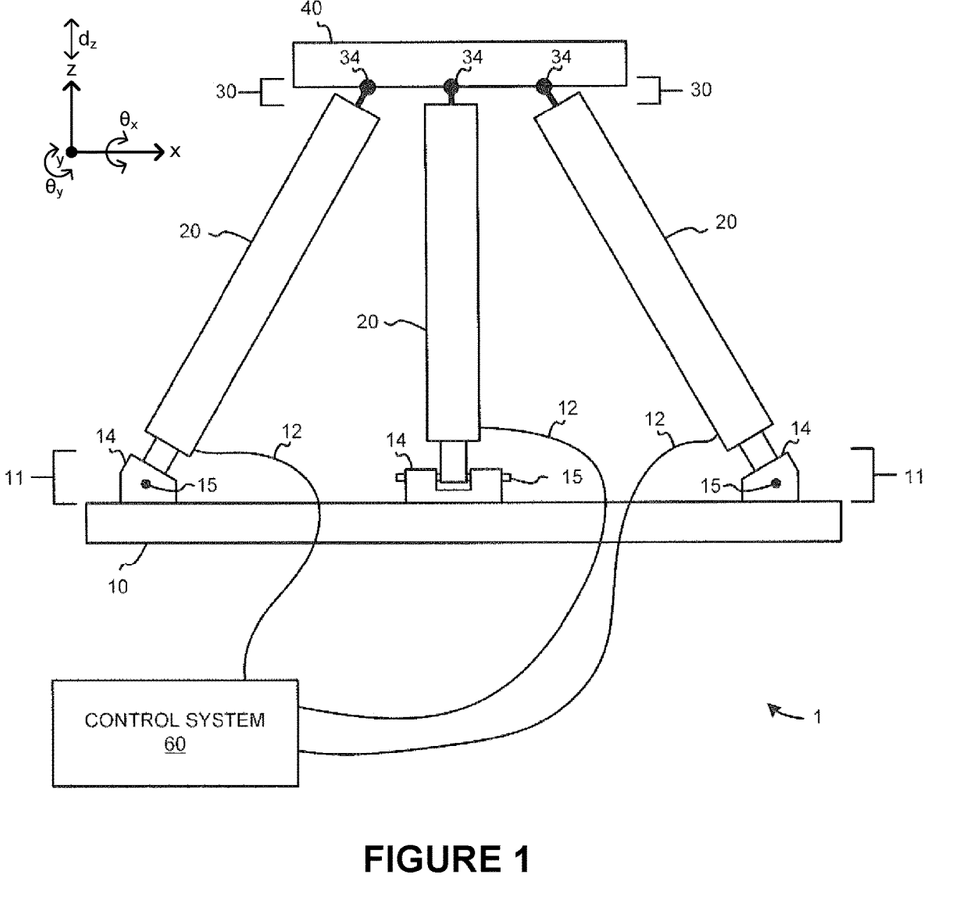
FIG. 1 shows an exemplary tripod parallel kinematic precision motion system.

FIG. 1 shows an exemplary tripod parallel kinematic precision motion system 1. The tripod motion system 1 comprises a bottom plate 10, a top plate 40 that is generally initially parallel to the bottom plate 10 in orientation, such as where the tripod motion system 1 is not actuated, and three linear actuators 20 coupled between the top plate 40 and the bottom plate 10. A linear actuator 20 includes a bottom single-degree-of-freedom (SDOF) hinge 11 of the bottom plate 10 and a top three-degrees-of-freedom (TDOF) joint 30 of the top plate 40. The tripod motion system 1 can be used to move, position, hold, and/or orient a workpiece. The three linear actuators 20 can be actuated to raise or lower the top plate 40, i.e., can move the top plate 40 along a Z-axis (see legend in the figure). The three linear actuators 20 can be actuated to tilt the top plate 40 to various degrees of incline and in any direction, i.e., can move the top plate 40 along one or more of the X-axis, the Y-axis, and/or the Z-axis.

The three linear actuators 20 can move the top plate 40 in a linear motion $D_Z$ along the Z-axis. The three linear actuators 20 can move the top plate 40 in a rotational motion to tilt/rotate about the X-axis in a $\theta_X$ motion. The three linear actuators 20 can move the top plate 40 in a rotational motion to tilt/rotate about the Y-axis in a $\theta_Y$ motion.

The three linear actuators 20 are configured to lengthen or shorten over a linear actuation span. The three linear actuators 20 can be singly actuated, wherein only one linear actuator of the three linear actuators 20 is actuated at one time. Alternatively, the three linear actuators 20 can be multiply actuated, wherein two or three linear actuators are actuated at one time. The three linear actuators 20 can be actuated in the same direction, i.e., all three linear actuators 20 could be lengthened). Alternatively, the three linear actuators 20 can be actuated in opposing directions, with one or more linear actuators 20 shortening and a different one or more lengthening at the same time.

The three linear actuators 20 can be actuated to move the top plate 40 to a predetermined set position with respect to the bottom plate 10. The predetermined set position can vary according to conditions. The predetermined set position can vary according to the operation being performed by the tripod motion system 1. The predetermined set position can vary according to a sequence of operations being performed by the tripod motion system 1. After moving the top plate 40 to a predetermined set position, the three linear actuators 20 can thereafter maintain the top plate 40 at the set position.

The bottom plate 10 includes the three spaced-apart bottom SDOF hinges 11. The bottom portion of a linear actuator 20 interacts with a corresponding bottom SDOF hinge 11 on the bottom plate 10. A bottom SDOF hinge 11 allows a linear actuator 20 to pivot with respect to the bottom plate 10, but only in a SDOF motion.

In the example shown, each bottom SDOF hinge 11 comprises a hinge block or blocks 14 affixed to or formed as part of the bottom plate 10. A pivot pin 15 extends between the hinge block(s) 14. The bottom portion of the linear actuator 20 fits over the pivot pin 15, allowing the linear actuator 20 to pivot in a SDOF pivoting motion with respect to the bottom plate 10. The pivot pin 15 in one example is affixed to the hinge block(s) 14, wherein the bottom portion of the linear actuator 20 rotates about the pivot pin 15. Alternatively, the pivot pin 15 can be affixed to the bottom portion of the linear actuator 20, wherein the pivot pin 15 rotates within the hinge block(s) 14. Consequently, via the pivot pin 15, the linear actuator 20 can pivot with a SDOF motion and over a range of angular movement. Therefore, the linear actuator 20 can only pivot in a planar arc with respect to the bottom plate 10.

The top plate 40 includes the three spaced-apart top TDOF joints 30 that interact with the three linear actuators 20. The top TDOF joints 30 enable the linear actuators 20 to move with three rotational degrees of freedom with respect to the top plate 40. This includes the linear actuator 20 being able to rotate with respect to the top plate 40, pivot in a X-Z plane, and pivot in a Y-Z plane.

Figure 10:
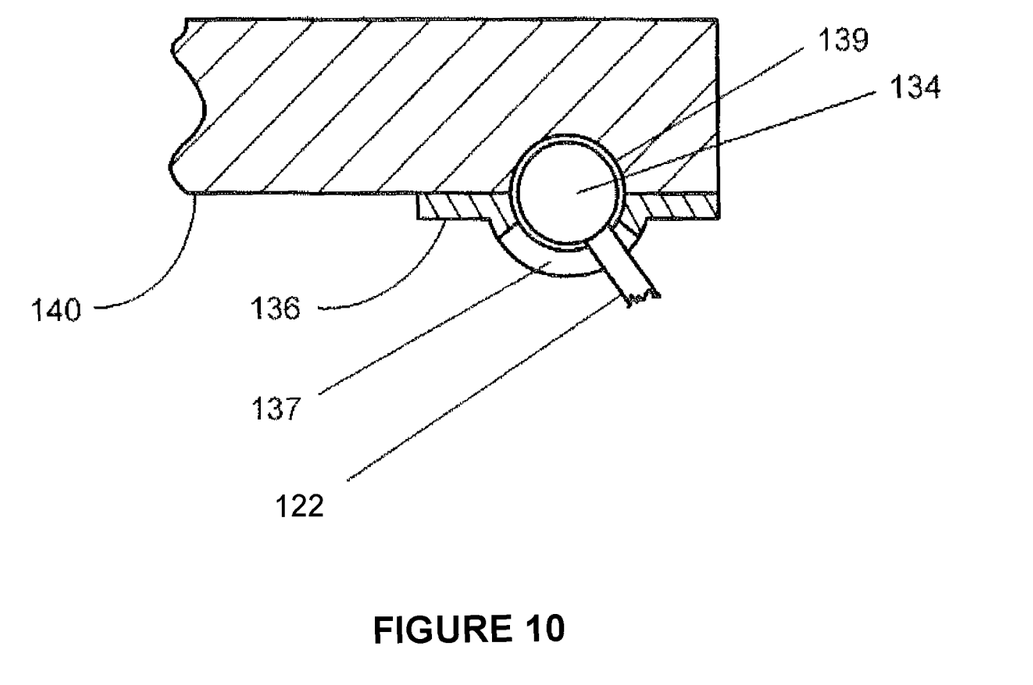
FIG. 10 shows detail of a top TDOF joint.

The ball 34 fits to a corresponding ball joint socket formed on the underside of the top plate 40 (see FIG. 10 and the accompanying text). Each top TDOF joint 30 of the top plate 40 includes a semi-spherical chamber 39 that receives and holds the ball 34 of the linear actuator 20. Consequently, via the ball 34, the linear actuator 20 can move with a TDOF motion and over ranges of angular movement, in addition to rotation of the ball 34. The linear actuator 20 therefore can rotate about its own axis or can move in an X-Z plane or in a Y-Z plane in the example shown, or in combinations thereof. Although a ball joint is shown in the example, it should be understood that any suitable joint mechanism with three degrees of freedom can be used, such as a cardan joint/U-joint combined with a rotational joint, for example.

Each linear actuator 20 receives a set position signal and generates a set position for the tripod motion system 1. The set position comprises a position that is supposed to be achieved and held by the linear actuator 20. As previously discussed, the three linear actuators 20 may have the same set position or may differ, depending on the desired position and orientation of the top plate 40. The three linear actuators 20 are coupled to a control system 60 by lines 12. The lines 12 communicate a set position signal or signals in some examples. The lines 12 provide power to the three linear actuators 20 in some examples, wherein the provided power is used to hold or achieve a set position in each linear actuator 20.

An actuation method for the tripod motion system 1 comprises receiving a predetermined set position to be achieved by the tripod motion system, with the predetermined set position including three set positions for three linear actuators 20 of the tripod motion system 1, and moving a linear actuator 20 to the predetermined set position, with each linear actuator 20 of the three linear actuators being coupled to a bottom SDOF hinge 11 on the bottom plate 10 of the tripod motion system 1 and being further coupled to a top TDOF joint 30 on the top plate 40 of the tripod motion system 1.

The three linear actuators 20 can be configured to retract or extend by very small and very precise linear extension increments. In some examples, the three linear actuators 20 can be configured to move in retraction or extension increments that have an actuation displacement tolerance of microns or sub-microns, wherein the top plate 40 can be positioned with a very high degree of accuracy.

The actuation tolerances of the linear actuators 120 in the tripod motion system 1 can be less than about 1-5 microns per 100 millimeters (mm) of travel in some examples. Various calibration methods can be used to further improve the geometric performance.

Rotational movements $\theta_X$ and $\theta_Y$ around the X-axis and the Y-axis, and linear movements along the Z-axis are decoupled in the tripod motion system 1. Due to the decoupled nature of the motion with respect to the X, Y, and Z axes, as well as the reduced error sources, calibration of the tripod motion system 1 enables sub-micron movement accuracy.

Figure 2:
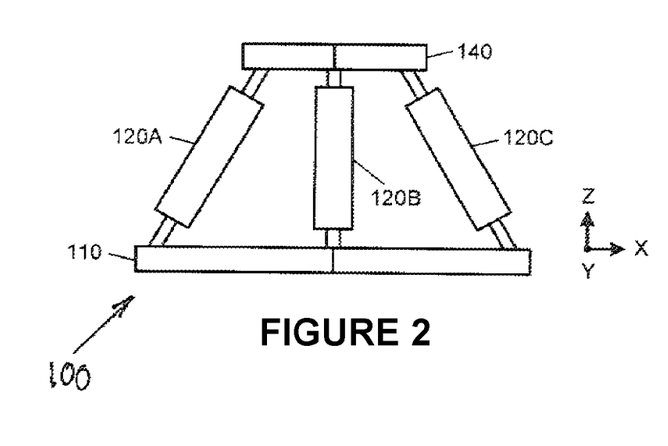
FIG. 2 shows the tripod motion system wherein the top plate is substantially horizontal.

FIG. 2 shows the tripod motion system 100 wherein the top plate 140 is substantially horizontal. As a result, the three linear actuators 120 are all of substantially the same length.

Figure 3:
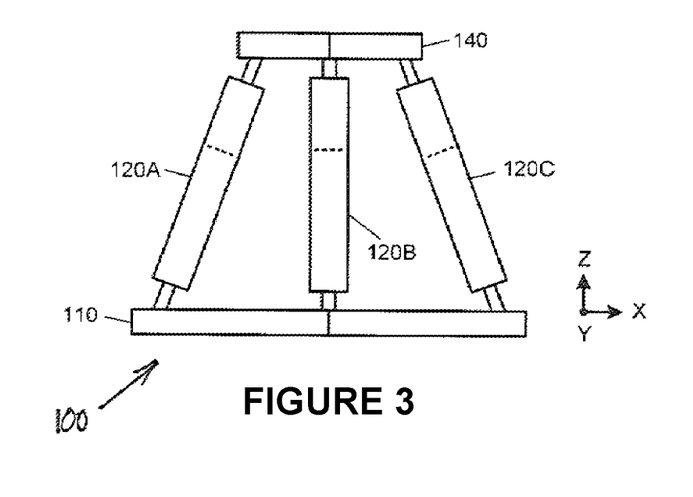
FIG. 3 shows the tripod motion system wherein the top plate has been displaced vertically.

FIG. 3 shows the tripod motion system 100 wherein the top plate 140 has been displaced vertically, i.e., along the Z-axis. To displace the top plate 140 along the Z-axis, all three linear actuators 120 are equally lengthened or shortened. The dashed lines in the linear actuators 120A-120C show the original displacement positions, wherein each actuator is lengthened by an equal amount to vertically displace the top plate 140.

Figure 4:
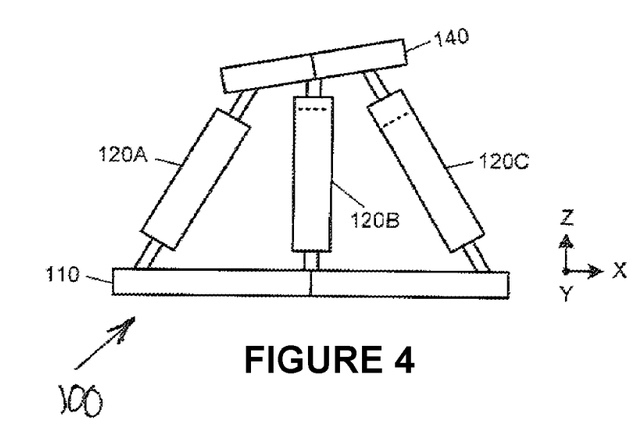
FIG. 4 shows the tripod motion system wherein the top plate has been tilted to the left.

FIG. 4 shows the tripod motion system 100 wherein the top plate 140 has been tilted to the left in the figure. To tilt the top plate 140, the three linear actuators 120 can be actuated to different displacement lengths. The top plate 140 can be tilted independently of movement along the Z-axis, but also can be performed in conjunction with movement along the Z-axis. The tilt can be achieved in multiple ways. The tilt can be achieved by lengthening one or two linear actuators of the three linear actuators 120. The tilt can be achieved by shortening one or two linear actuators of the three linear actuators 120. The tilt can be achieved by lengthening one or two of the linear actuators and also shortening two or one of the remaining linear actuators, wherein all three linear actuators may be changed from an initial length.

In the example in the figure, the linear actuator 120A has not been changed and is the same length as the starting position shown in FIG. 2. The linear actuator 120B has been lengthened somewhat, as indicated by the dashed line indicating the starting length. The linear actuator 120C has been lengthened more than the linear actuator 120B, as indicated by the dashed line. As a result, the top plate 140 is now tilted to the left (but the front-to-back tilt angle has not been changed). It should be understood that if the actuator 120B had also been left unchanged and if only the linear actuator 120C had been lengthened, then the top plate 140 would also tilt toward the front in the figure, in addition to tilting to the left.

Figure 5:
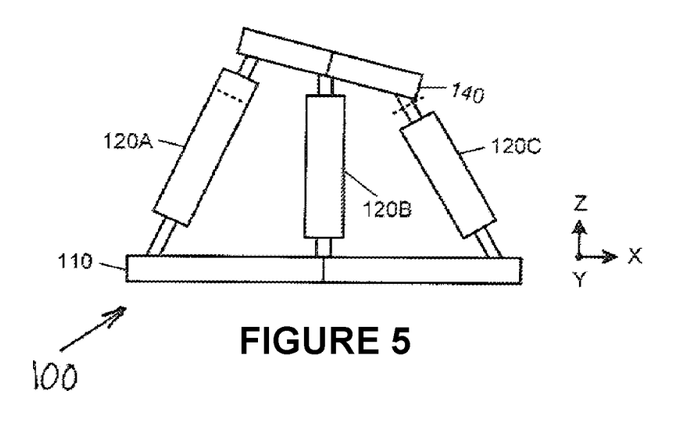
FIG. 5 shows the tripod motion system wherein the top plate has been tilted to the right.

FIG. 5 shows the tripod motion system 100 wherein the top plate 140 has been tilted to the right in the figure. In this example, the linear actuator 120B has not been changed and is the same length as the starting position shown in FIG. 2. The linear actuator 120A has been lengthened, as indicated by the dashed line indicating the starting length. Conversely, the linear actuator 120C has been shortened, as indicated by the dashed line.

Figure 6:
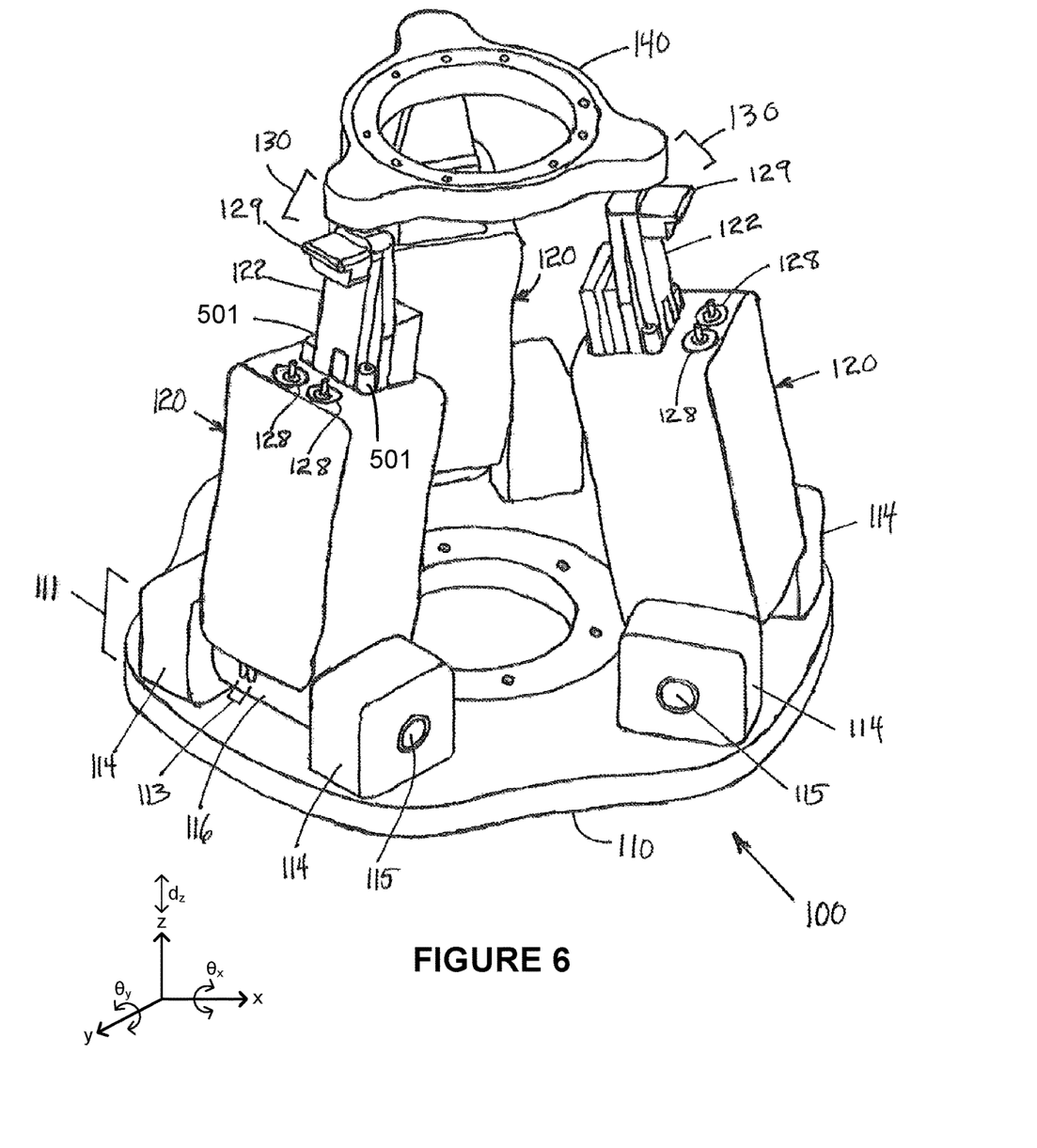
FIG. 6 shows an exemplary tripod parallel kinematic precision motion system.

FIG. 6 shows an exemplary tripod parallel kinematic precision motion system 100. The tripod motion system 100 comprises a bottom plate 110, a top plate 140, and three linear actuators 120 coupled between the top plate 140 and the bottom plate 110. The tripod motion system 100 can be used to move, position, hold, and/or orient a workpiece, as previously discussed.

The three linear actuators 120 can move the top plate 140 in a linear motion $D_X$ along the Z-axis. The three linear actuators 120 can move the top plate 140 in a rotational motion to tilt/rotate about the X-axis in a $θ_X$ motion. The three linear actuators 120 can move the top plate 140 in a rotational motion to tilt/rotate about the Y-axis in a $θ_Y$ motion.

A linear actuator 120 includes an actuator body 121, a bottom hinge portion 116 that interacts with a bottom SDOF hinge 111 of the bottom plate 110, a ball 134 positioned at the top end of the actuator slider 122 (see FIGS. 7-8), and an actuator flange 129 projecting from a top region of the actuator slider 122. A linear actuator 120 further includes a positioning actuator 124 that is configured to extend from and retract into the actuator body 121, linearly displacing the actuator slider 122 and the actuator flange 129. A linear actuator 120 further includes one or more displacing actuators 128 that act against the actuator flange 129. The actuator flange 129 is configured to be contacted by the one or more displacing actuators 128 and receive the actuation force(s) generated by the one or more displacing actuators 128. The one or more displacing actuators 128 provide a majority of force to hold the linear actuator 120 at a set position.

The positioning actuator 124 receives a set position signal and generates a set position for the tripod motion system 100. The set position comprises a position that is supposed to be achieved and held by the linear actuator 120, i.e., the position/actuation length that the linear actuator 120 should achieve. As previously discussed, the three linear actuators may have the same set position or may differ, depending on the desired position and orientation of the top plate 140. The set position signal can be received from a controller device or other external source (not shown). The set position signal can comprise any manner of appropriate signal, including any appropriate mechanical, electrical, magnetic, optical, or pneumatic linear position signal.

The positioning actuator 124 generates an extension force that extends or retracts the slider 122, which holds the ball 134. The positioning actuator 124 can be configured to retract or extend by very small and very precise linear extension increments. In some examples, the positioning actuator 124 can be configured to move in retraction or extension increments that have an actuation displacement tolerance of microns or sub-microns, wherein the top plate 140 can be positioned with a very high degree of accuracy. However, the positioning actuator 124 may not generate enough actuation force to hold or move the top plate 140 against steady-state load forces such as gravity.

In one example, the positioning actuator 124 comprises an electric positioning component, wherein an electric current is supplied to the positioning actuator 124 in order to hold or move the actuator slider 122. In another example, the positioning actuator 124 comprises a linear electric motor, wherein an electric current is supplied to the positioning actuator 124 in order to hold or move the actuator slider 122 and wherein the linear electric motor is configured to move the actuator slider 122 by predetermined linear actuation increments. In yet another example, the positioning actuator 124 comprises a motor and rotational actuator device, such as a lead screw.

The positioning actuator 124 may be able to move the ball 134 to, and hold at, a predetermined extension position (or set position) when there is no load or force on the top plate 140. In addition, the positioning actuator 124 will return to the predetermined set position if an external force displaces the top plate 140. However, the positioning actuator 124 is not designed to provide all of the hold or extension force that is generated by a linear actuator 120. Instead, the positioning actuator 124 of a linear actuator 120 is designed to move the ball 134 to a predetermined extension position.

The positioning actuator 124 receives a position command and moves the actuator slider 122 to a predetermined set position as given by the position command. The position command is received from a controller or other external device, such as the positioning controller 170 of FIG. 11, for example. However, the positioning actuator 124 does not exert a majority of the force needed to position or hold the top plate 140 at the predetermined set position.

The one or more displacing actuators 128 act against the actuator flange 129. The one or more displacing actuators 128 operate to provide a majority of the force that is needed to position and hold the top plate 140 at the predetermined set position. The one or more displacing actuators 128 can supply more force to the top plate 140 than the positioning actuator 124 can supply. The one or more displacing actuators 128 can provide the force without electrical power consumption and without heating up the linear actuator 120. In addition, the one or more displacing actuators 128 can counteract a disturbance of the top plate 140 due to external forces.

The one or more displacing actuators 128 are configured to generate actuation forces against the actuator flange 129. The one or more displacing actuators 128 are configured to generate actuation forces that add to the actuation force supplied by the positioning actuator 124. The one or more displacing actuators 128 are configured to generate actuation forces that add to the actuation forced supplied by the positioning actuator 124 in order to maintain the actuator slider 122 at the set position that is set by the positioning actuator 124. The one or more displacing actuators 128 are configured to support the load against gravity. Further, the one or more displacing actuators 127 assist the positioning actuator 124 in the event that an external force or forces acts on the tripod motion system 100.

The one or more displacing actuators 128 extend to contact the actuator flange 129. The one or more displacing actuators 128 generate actuation forces on the actuator flange 129 and the actuator slider 122, supporting the set position as set by the positioning actuator 124. The one or more displacing actuators 128 generate the actuation forces based on a pneumatic pressure, in some examples. Alternatively, in other examples, the one or more displacing actuators 128 can comprise magnetic actuator devices or mechanical spring actuator devices, for example.

The one or more displacing actuators 128 in some examples comprise pneumatic actuators including a piston chamber, a piston configured to reciprocate within the piston chamber, and a piston rod coupled to the piston and extending out of the pneumatic actuator 128. A pneumatic port (not shown) introduces pneumatic air into the one or more displacing actuators 128, below the internal piston, wherein the pneumatic air displaces the piston upward and extends the piston rod.

The amount of actuation force generated by the one or more displacing actuators 128 will depend on the pneumatic pressure provided to the one or more displacing actuators 128 by an external pneumatic source. The pneumatic pressure is calibrated according to the weight of the expected load to be placed on and supported by the top plate 140. Alternatively, the pneumatic pressure is calibrated according to the weight of the expected load on the top plate 140 minus an actuation force generated by the positioning actuator 124. However, the actuation force generated by the one or more displacing actuators 128 may be much greater than the actuation force generated by the positioning actuator 124, wherein the actuation force generated by the positioning actuator 124 may be neglected in choosing the pneumatic pressure.

The three linear actuators 120 do not require a large amount of electrical power to hold the set position. The low electrical power consumption of a positioning actuator 124 of a linear actuator 124 minimizes heating of the linear actuator 120. The one or more displacing actuators 128 provide a majority of force to hold the linear actuator 120 at a set position. The one or more displacing actuators 128 make the load essentially weightless and the positioning actuator 124 supplies an additional force to change the position of the top plate 140 and the load. It is an advantage that the three linear actuators 120 will return the top plate 140 to the set position after the top plate 140 is disturbed or displaced by an external force. It is an advantage that the three linear actuators 120 (and the tripod motion system 100) can be designed and configured to achieve a sub-micron positioning accuracy of the top plate 140.

The bottom plate 110 includes three spaced-apart bottom single-degree-of-freedom (SDOF) hinges 111. The bottom hinge portion 116 of a linear actuator 120 interacts with a corresponding bottom SDOF hinge 111 on the bottom plate 110. A bottom SDOF hinge 111 allows a linear actuator 120 to pivot with respect to the bottom plate 110, but only in a SDOF motion.

In the example shown, each bottom SDOF hinge 111 comprises two hinge blocks 114 affixed to or formed as part of the bottom plate 110. A pivot pin 115 extends between the two hinge blocks 114. The bottom hinge portion 116 of the linear actuator 120 fits over the pivot pin 115, allowing the linear actuator 120 to pivot in a SDOF pivoting motion with respect to the bottom plate 110. The pivot pin 115 in one example is affixed to the two hinge blocks 114, wherein the bottom hinge portion 116 of the linear actuator 120 rotates about the pivot pin 115. Alternatively, the pivot pin 115 can be affixed to the bottom hinge portion 116, wherein the pivot pin 115 rotates within the two hinge blocks 114. Consequently, via the pivot pin 115, the linear actuator 120 can pivot with a SDOF motion and over a range of angular movement. Therefore, the linear actuator 120 can only pivot in a planar arc with respect to the bottom plate 110. Alternatively, the bottom SDOF hinges 111 can comprise any mechanism that allows movement in a single degree of freedom, such as bearings, for example.

The top plate 140 includes three spaced-apart top three-degree-of-freedom (TDOF) joints 130 that interact with the three linear actuators 120. The top TDOF joints 130 enable the linear actuators 120 to move with three rotational degrees of freedom with respect to the top plate 140. This includes the linear actuator 120 being able to rotate with respect to the top plate 140, pivot in a X-Z plane, and pivot in a Y-Z plane.

The ball 134 fits to a corresponding ball joint socket formed on the underside of the top plate 140 (see FIG. 10 and the accompanying text). Each top TDOF joint 130 of the top plate 140 includes a semi-spherical chamber 139 that receives and holds the ball 134 of the linear actuator 120. Consequently, via the ball 134, the linear actuator 120 can move with a TDOF motion and over ranges of angular movement, in addition to rotation of the ball 134. The linear actuator 120 therefore can rotate about its own axis or can move in an X-Z plane or in a Y-Z plane in the example shown, or in combinations thereof. Alternatively, the top TDOF joints 130 can comprise cardan joints/U-joints combined with a rotational joint or any other suitable mechanism that allows three degrees of freedom of movement.

The actuation tolerances in the linear actuators 120 of the tripod motion system 100 can be less than about 1-5 microns per 100 millimeters (mm) of travel in some examples. Various calibration methods can be used to further improve the geometric performance.

Rotational movements around the X-axis and the Y-axis, and linear movements along the Z-axis are decoupled in the tripod motion system 100. Due to the decoupled nature of the motion with respect to the X, Y, and Z axes, as well as the reduced error sources, calibration of the tripod motion system 100 enables sub-micron movement accuracy.

An actuation method for the tripod motion system 100 comprises receiving a predetermined set position to be achieved by the tripod motion system, with the predetermined set position including three set positions for three linear actuators of the tripod motion system, moving a positioning actuator of a linear actuator substantially to the corresponding predetermined set position, with each linear actuator of the three linear actuators being coupled to a bottom single-degree-of-freedom (SDOF) hinge on a bottom plate of the tripod motion system and being further coupled to a top three-degrees-of-freedom (TDOF) joint on a top plate of the tripod motion system, and moving one or more displacing actuators of the linear actuator to boost the linear actuator and to hold the linear actuator at the predetermined set position, with the one or more displacing actuators of the linear actuator providing a majority of a displacement force generated by the linear actuator.

Figure 7:
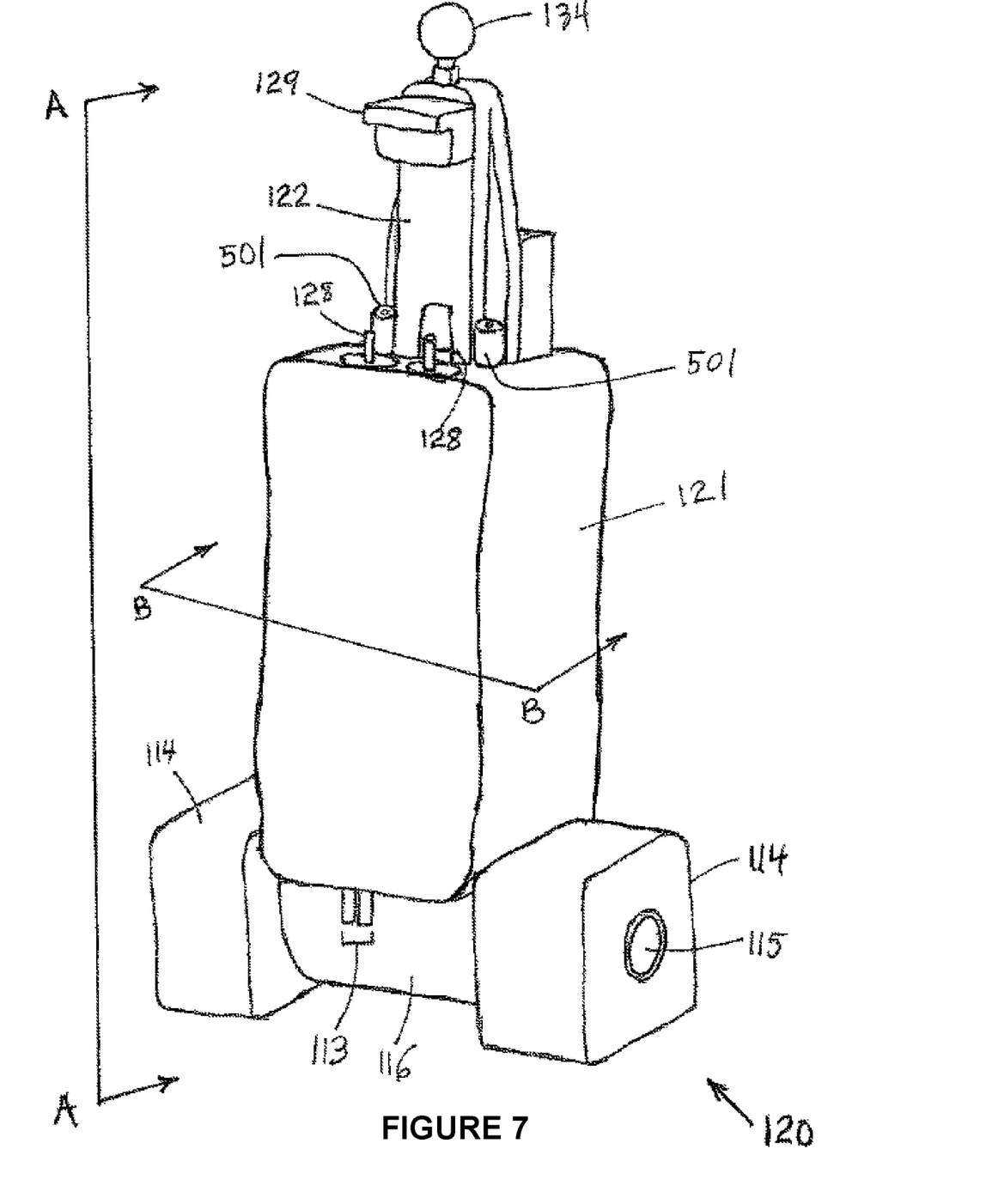
FIG. 7 shows detail of an exemplary linear actuator.

FIG. 7 shows detail of an exemplary linear actuator 120. The linear actuator 120 includes the bottom hinge portion 116 that fits around the pivot pin 115. Connectors 113 extend from the actuator body 121 in the region of the bottom hinge portion 116. The connectors 113 in one example comprise electrical and pneumatic connectors that supply electrical power and pneumatic power to the linear actuator 120. In addition, the connectors 113 can provide control signals to the linear actuator 120. The figure shows the ball 134 that comprises a portion of the top TDOF joint 130. The figure also shows the actuator flange 129. The actuator flange 129 is affixed to the top region of the actuator slider 122. The actuator flange 129 can be affixed to the actuator slider 122 in any suitable manner, including using adhesives or bonding agents, welds, clips, latches, or fasteners. In the example, the one or more displacing actuators 128 comprise two displacing actuators 128. The two displacing actuators 128 in the figure are not currently pressurized with pneumatic air, and consequently the two displacing actuators 128 do not extend upwards and contact the actuator flange 129.

Figure 8:
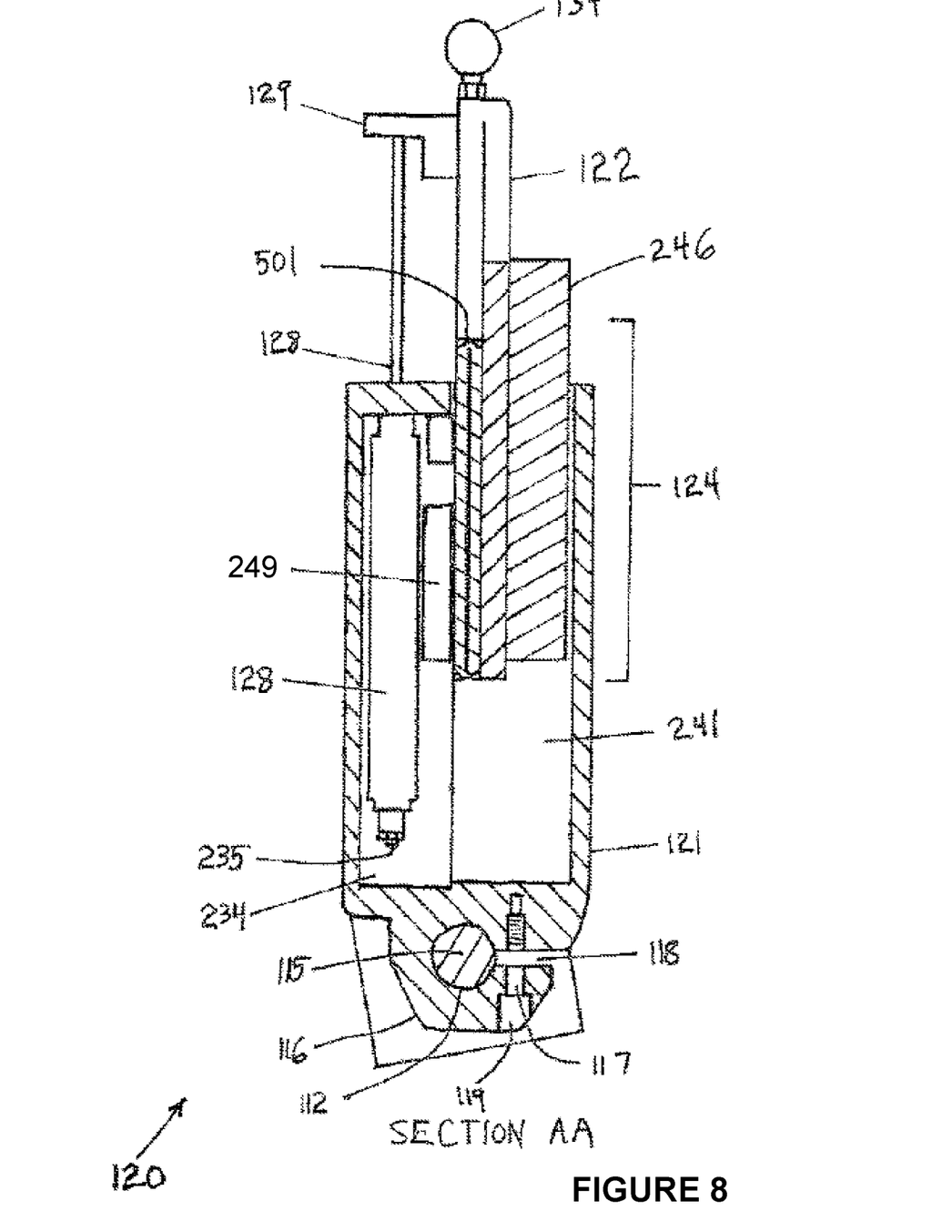
FIG. 8 is a cross-section view of a linear actuator.

FIG. 8 is a cross-section view AA of the linear actuator 120 of FIG. 7. It can be seen from the figure that the bottom hinge portion 116 includes a pin aperture 112 for receiving the pivot pin 115. The pin aperture 112 further includes a compression gap 118 that allows the pin aperture 112 to be constricted, wherein the bottom hinge portion 116 can be clamped onto the pivot pin 115. The pin aperture 112 further includes a threaded bore 117 and countersink 119 for receiving a threaded fastener (not shown), wherein the threaded fastener can be manipulated to constrict the compression gap 118.

The actuator body 121 includes a displacing actuator chamber 234 that receives the one or more displacing actuators 128. The number of displacing actuators 128 can be chosen according to the desired displacing actuator force to be placed on the actuator flange 129 in some examples, wherein the number of displacing actuators can be increased where an increased displacing actuator force is desired. A pneumatic conduit 235 passes into the displacing actuator chamber 234 and is coupled to the one or more displacing actuators 128. The pneumatic conduit 235 provides pneumatic pressure to the one or more displacing actuators 128. The piston rods of the one or more displacing actuators 128 extend up through the top of the actuator body 121 and can contact the underside of the actuator flange 129, supplying a displacing force to the actuator slider 122.

The actuator body 121 further includes a positioning actuator chamber 241 that receives the positioning actuator 124. The positioning actuator chamber 241 can comprise a separate chamber from the displacing actuator chamber 234, or can be at least partially open to the displacing actuator chamber 234.

The positioning actuator 124 in the example shown comprises a linear electric motor. The positioning actuator 124 includes a magnetic body 246 affixed to the actuator slider 122 and a stationary component comprising a coil assembly 247 (see FIG. 9) affixed to the actuator body 121. The coil assembly 247 acts on the magnetic body 246 when energized. The coil assembly 247 can cause the actuator slider 122 to be extended farther from the actuator body 121. Conversely, the coil assembly 247 can cause the actuator slider 122 to be further retracted into the actuator body 121. Electrical conductors (not shown), such as wires or cables, can extend into the positioning actuator chamber 241 to the coil assembly 247.

Figure 11:
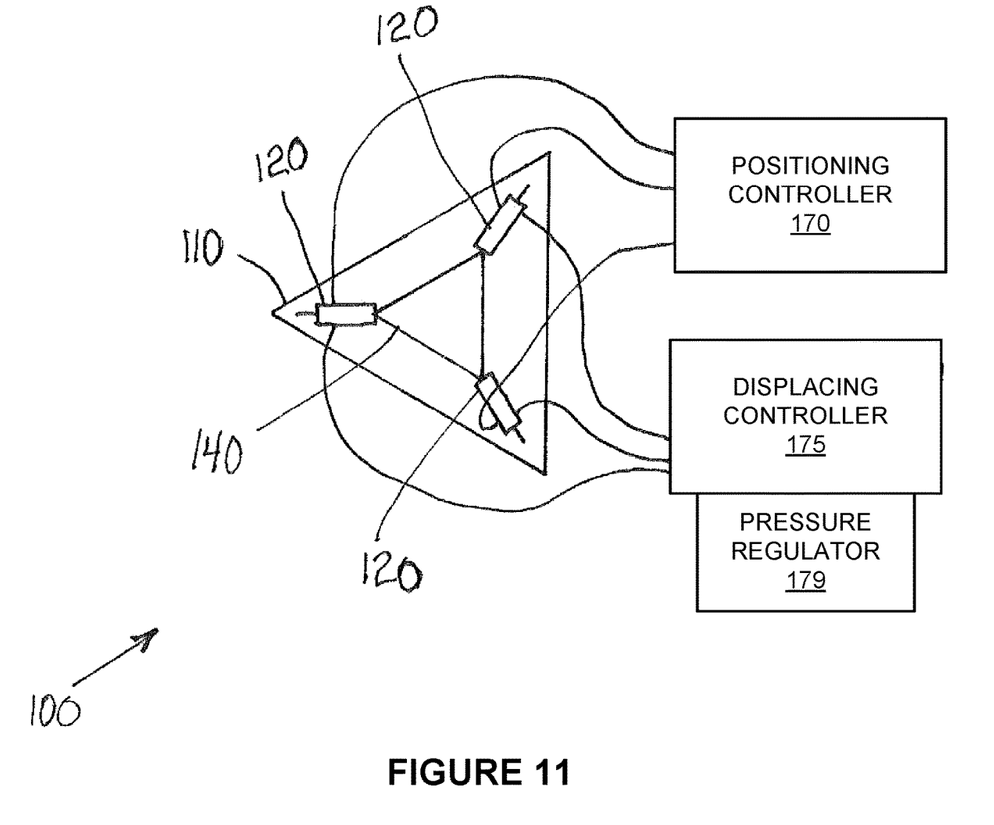
FIG. 11 shows the tripod motion system in an operational environment.

The positioning actuator 124 further includes a positional feedback device 249 that generates a positional signal that is provided to the coil assembly 247 (or is provided to a positioning controller 170 that operates the coil assembly 247, see FIG. 11). The positional feedback device 249 generates a linear positional signal that is used to actuate the positioning actuator 124. The positional feedback device 249 generates the positional signal based on the linear position of the actuator slider 122 (see FIG. 9 and the accompanying discussion below). The positional feedback device 249 is able to sense and move to position increments that have an error tolerance of microns or sub-microns.

In one example, the positional feedback device 249 comprises a magnetic sensor, including a Hall Effect sensor. Alternatively, the positional feedback device 249 can comprise an optical, electrical, or mechanical sensor or other position sensor that generates a suitable positional signal.

Figure 9:
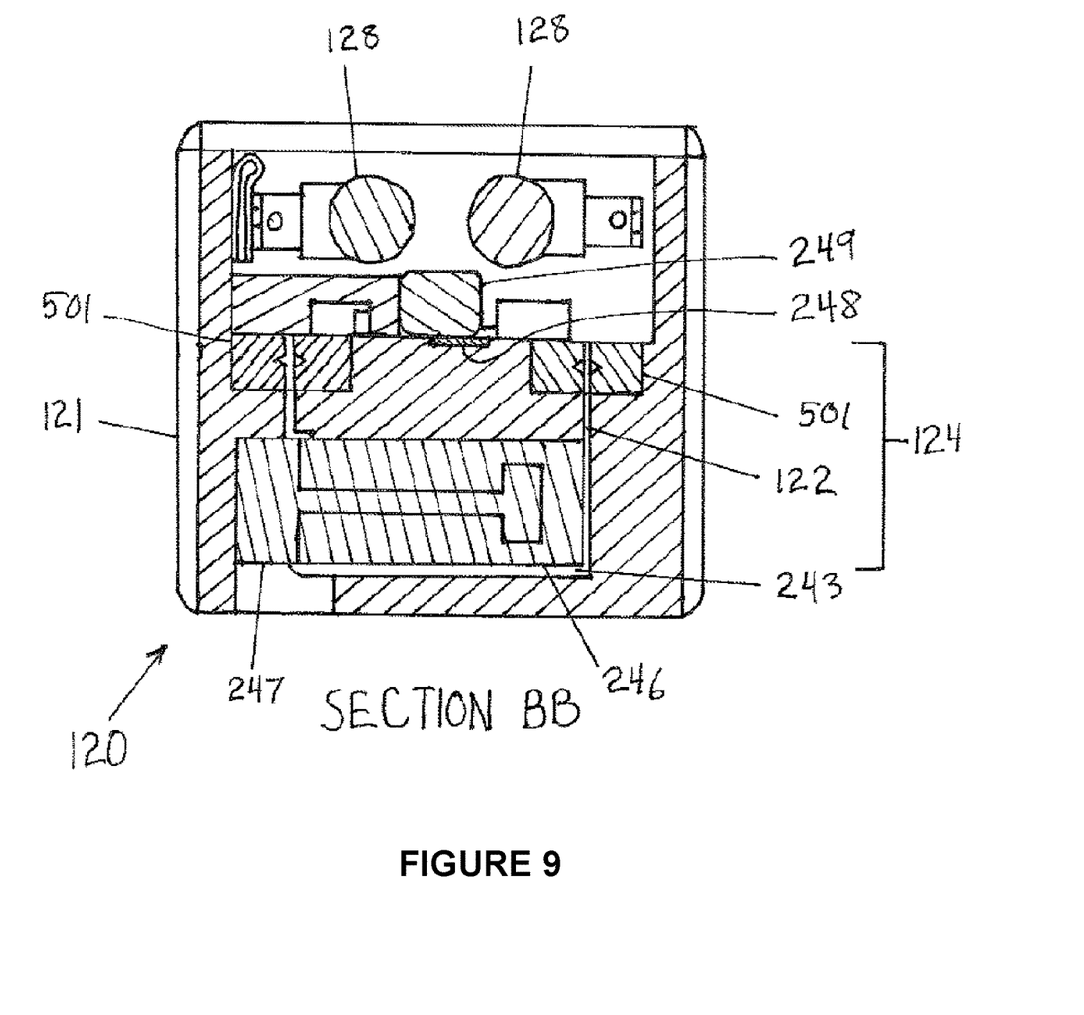
FIG. 9 is a cross-section view of the linear actuator.

FIG. 9 is a cross-section view BB of the linear actuator 120 of FIG. 7. This figure shows the components of the positioning actuator 124 in one example. The positioning actuator 124 in this example includes the actuator slider 122, a magnetic body 246 affixed to the actuator slider 122, and a coil assembly 247 that corresponds in shape to the magnetic body 246. The coil assembly 247 acts on the magnetic body 246 when energized and generates magnetic force on the magnetic body 246, wherein the magnetic body 246 moves the actuator slider 122.

Roller bearings 501 are located on the sides of the actuator slider 122. The roller bearings 501 allow the actuator slider 122 to move smoothly up and down within the actuator body 121.

The linear actuator 120 further includes an encoder grating 248 affixed to the actuator slider 122. A positional feedback device 249 is affixed to the actuator body 121 and interacts with the encoder grating 248 to generate a linear positional feedback signal. The positional feedback signal corresponds to the position of the actuator slider 122.

FIG. 10 shows detail of a top TDOF joint 130. Each top TDOF joint 130 includes a semi-spherical ball chamber 139 formed in the top plate 140 and a ball retainer plate 136 held to the top plate 140. The ball retainer plate 136 is affixed to the top plate 140. The ball retainer plate 136 can be affixed to the top plate 140 in any suitable manner, including using adhesives or bonding agents, welds, clips, latches, or fasteners. The ball retainer plate 136 also includes a semi-spherical chamber, wherein the semi-spherical chamber 139 and the ball retainer plate 136 together trap and hold the ball 134 of the linear actuator 120. The ball retainer plate 136 includes an opening 137 that allows the actuator slider 122 to move over a predetermined range of motions as the ball 134 rotates within the semi-spherical chamber 139 of the top plate 140. As a result, the linear actuator 120 can move with a TDOF motion and over ranges of angular movement, in addition to rotation of the ball 134. The linear actuator 120 therefore can rotate about its own axis or can move in an X-Z plane or in a Y-Z plane in the example shown, or in combinations thereof.

FIG. 11 shows the tripod motion system 100 in an operational environment. The tripod motion system 100 further includes a positioning controller 170 that is coupled to the positioning actuators 124 of the three linear actuators 120. The positioning controller 170 receives the positional signal that is generated by the positional feedback device 249. The positioning controller 170 processes the positional signal and transmits a control signal to the coil assembly. The control signal operates the coil assembly to put the positioning actuator 124 at the predetermined set position.

The tripod motion system 100 further includes a displacing controller 175 that operates the one or more displacing actuators 128. In some examples, the positioning controller 170 and the displacing controller 175 can comprise sub-components of a controller that controls all aspects of the tripod motion system 100, such as in the control system 60 of FIG. 1. The displacing controller 175 can includes a pneumatic air source coupled to the one or more displacing actuators 128 of each of the three linear actuators 120. The displacing controller 175 can regulate the provision of pneumatic air to the one or more displacing actuators 128. The displacing controller 175 can include various pneumatic components, including a cut-off valve, a pressure regulator, air dryers or filters, and any other needed components.

The displacing controller 175 in one example includes a pressure regulator 179 that supplies a substantially fixed pneumatic pressure to the one or more displacing actuators 128. The substantially fixed pneumatic pressure comprises a pneumatic pressure that is selected to enable the one or more displacing actuators 128 to hold the linear actuator 120 at the predetermined set position. The substantially fixed pneumatic pressure will be satisfactory for maintaining a predetermined set position wherein a load applied to the top plate 140 is relatively unvarying.

The displacing controller 175 in another example includes a controllable pressure regulator 179 that supplies a controllable pneumatic pressure to the one or more displacing actuators 128. The controllable pneumatic pressure comprises a pneumatic pressure that can be varied as needed in order to enable the one or more displacing actuators 128 to hold the linear actuator 120 at the predetermined set position. The controllable pneumatic pressure can be varied to accommodate loads that vary dynamically in weight. Alternatively, the pressure regulator 179 can be replaced by counterbalances.

The three linear actuators 120 are controlled by the positioning controller 170. The linear actuator motion can be independent or coordinated. Coordinated motion means that all linear actuators 120 are moved strategically in synchronized fashion with respect to time, not necessarily with respect to the same position, such that the three linear actuators 120 move the top plate 140 in a clearly defined and intended motion in the degrees of freedom in the linear motion $D_Z$ and in the rotational motions $\theta_X$, and $\theta_Y$. In order to have the linear actuators 120 move in the coordinated motion, the positioning controller 170 can calculate kinematic relationships of the linear actuators 120 based on theoretical or calibrated joint locations 34 and 15 (or 130 and 111). The kinematic equations can be processed in both a forward and inverse kinematic method to ensure both the ending location and the path taken to achieve the ending location are controlled and optimized in real time. The forward kinematics take the existing locations of the linear actuators 120 determined by the positional feedback device 249 and calculate the coordinate system axes of the top plate 140. The inverse kinematic equations take the desired end points in the coordinate system axes and calculate the desired position of each linear actuator which is used to drive the tripod motion system to that position. Both sets of kinematics are used to provide optimum performance, but both sets are not required.

Figure 12:
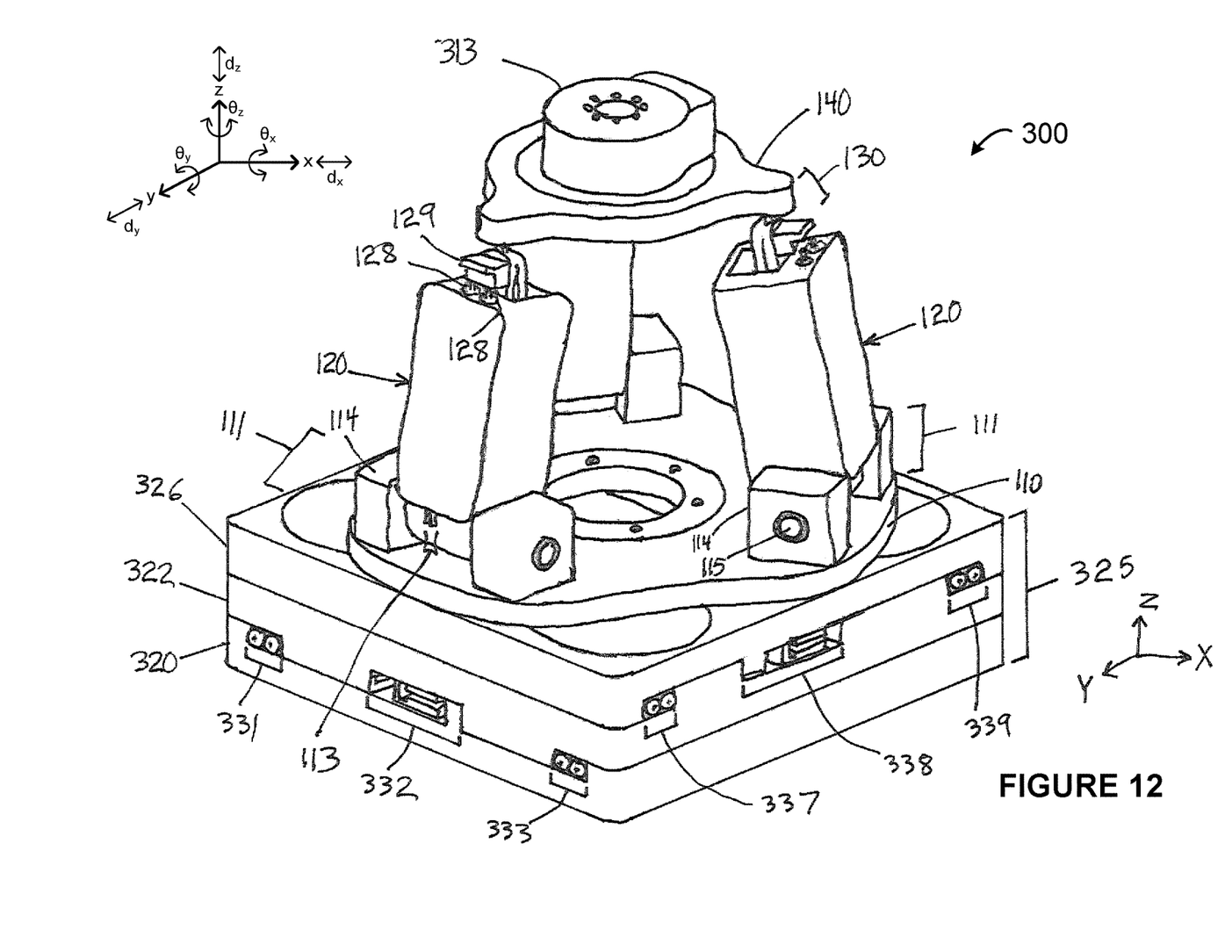
FIG. 12 shows an exemplary tripod motion system that provides six degrees of freedom of motion.

FIG. 12 shows an exemplary tripod motion system 300 that provides six degrees of freedom of motion. In addition to the previously recited components, the tripod motion system 300 includes a XY positioning table 325 affixed to one of the bottom plate 110 or the top plate 140 and a rotator component 313 affixed to one of the top plate 140 or the bottom plate 110. However, in some examples, both of the positioning table 325 and the rotator component 313 can be affixed to the top plate 140 or both can be affixed to the bottom plate 110. A workpiece can be affixed to the rotator component 313. The rotator component 313 and the positioning table 325 can be coupled to a controller that operates the tripod motion system 300, as previously discussed.

The rotator component 313 can rotate about the Z-axis in a $\theta_Z$ motion. The three linear actuators 120 can move the top plate 140 in a linear motion $D_Z$ along the Z-axis. The three linear actuators 120 can move the top plate 140 in a rotational motion to tilt/rotate about the X-axis in a $\theta_X$ motion. The three linear actuators 120 can move the top plate 140 in a rotational motion to tilt/rotate about the Y-axis in a $\theta_Y$ motion. The positioning table 325 can move the bottom plate 110 in a linear motion $D_X$ along the X-axis. The positioning table 325 can move the bottom plate 110 in a linear motion $D_Y$ along the Y-axis.

The rotator component 313 is configured to receive the workpiece and rotate the workpiece. The rotator component 313 is affixed to the top plate 140 and is configured to rotate about a Z-axis of the tripod motion system 300. The rotator component 313 can rotate through any amount of rotational displacement. The rotator component 313 can include a rotational feedback device (not shown). The rotational feedback device provides $\theta_Z$ rotational position information to a rotator controller 184 (see FIG. 13).

The positioning table 325 is affixed to the bottom plate 110. The positioning table 325 is configured to move the bottom plate 110 with respect to an X-axis and with respect to a Y-axis. The positioning table 325 is configured to move the bottom plate 110 in an X-direction. The positioning table 325 is configured to move the bottom plate 110 in a Y-direction. It should be understood that the positioning table 325 can simultaneously move the bottom plate 110 in both the X-direction and in the Y-direction.

The positioning table 325 in the example shown includes a bottom layer 320, a middle layer 322, and a top layer 326. Translation mechanisms 331, 332, and 333 are disposed between the bottom layer 320 and the middle layer 322. The translation mechanisms 331, 332, and 333 can include a rail or rails for allowing translation of the middle layer 322 in a Y-direction with respect to the bottom layer 320. The translation mechanisms 331, 332, and 333 can include a power transmission device or devices for translating the middle layer 322 in the Y-direction. Likewise, translation mechanisms 337, 338, and 339 are disposed between the middle layer 322 and the top layer 326. The translation mechanisms 337, 338, and 339 include a guide structure or structures for allowing translation motion of the top layer 326 in an X-direction with respect to the middle layer 322. The translation mechanisms 337, 338, and 339 can include a power transmission device or devices for translating the top layer 326 in the X-direction. In some examples, the translation mechanisms 337 and 339 comprise bearings and the translation mechanism 338 comprises a motor and actuator mechanism.

In addition, the positioning table 325 can include a position feedback device (not shown). The position feedback device provides X-axis and Y-axis positional feedback information to a table controller 186 (see FIG. 13).

It can be seen from the figure that the tripod motion system 300 can provide six degrees of freedom of movement to a workpiece affixed to the rotator component 313. The tripod motion system 300 can move the workpiece straight up and down, in a Z-direction. The tripod motion system 300 can move the workpiece front-to-back, in a Y-direction. The tripod motion system 300 can move the workpiece side-to-side, in an X-direction. The tripod motion system 300 can rotate the workpiece around the Z-axis. The tripod motion system 300 can tilt the workpiece with respect to the X-axis. The tripod motion system 300 can tilt the workpiece with respect to the Y-axis.

Figure 13:
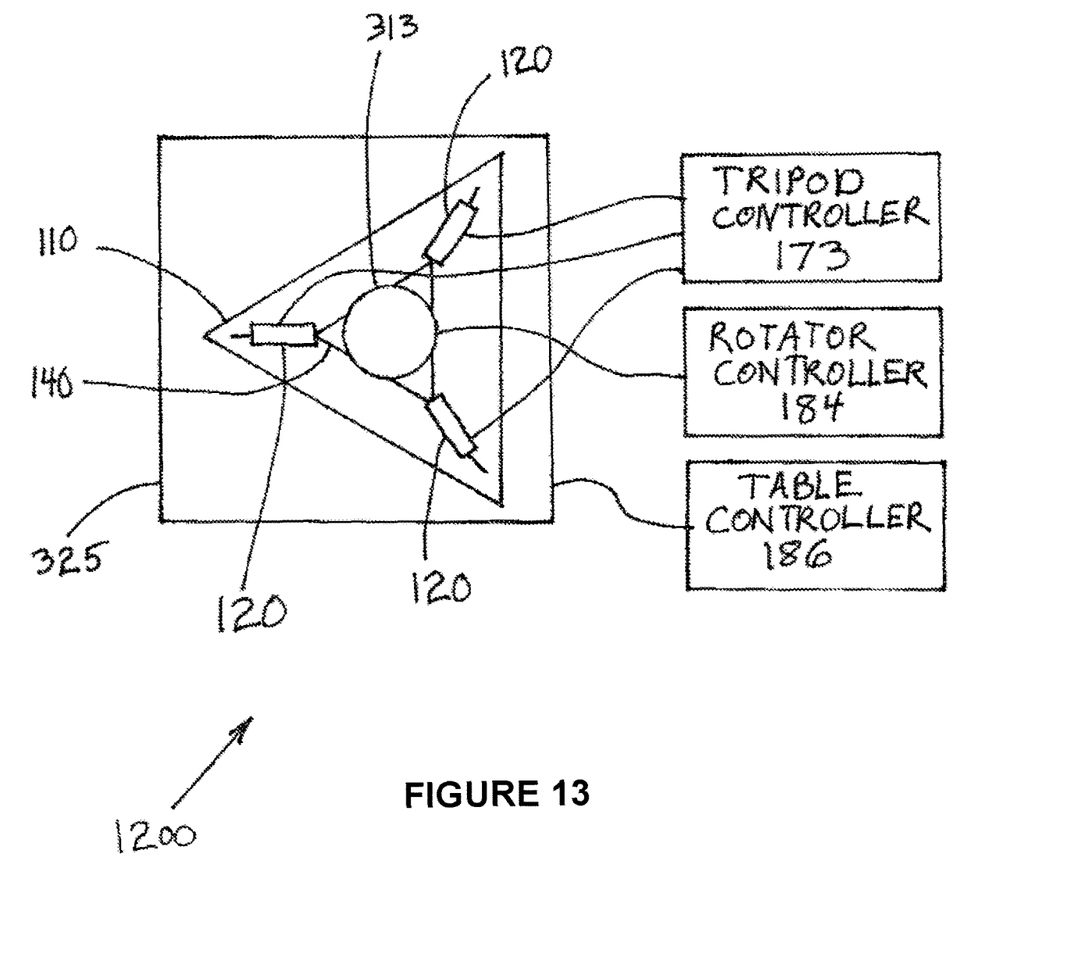
FIG. 13 shows the tripod motion system in an operational environment.

FIG. 13 shows a tripod motion system 1200 in an operational environment. The tripod motion system 1200 further includes a tripod controller 173 that is coupled to the three linear actuators 120, a rotator controller 184 that is coupled to the rotator component 313, and a table controller 186 that is coupled to the positioning table 325. The tripod controller 173 controls actuations of the three linear actuators 120 and can generate the rotational movements $\theta_X$ and $\theta_Y$ and can generate the linear movement $D_Z$. The rotator controller 184 controls actuation of the rotator component 313 and can generate the rotational movement $\theta_Z$. The table controller 186 controls actuations of the positioning table 325 and can generate the linear movements $D_X$ and $D_Y$. However, it should be understood that the tripod controller 173, the rotator controller 184, and the table controller 186 could alternatively be combined into a single controller or could be incorporated into other systems or components.

In some examples, an actuation method for a tripod motion system comprises the tripod motion system receiving a predetermined set position to be achieved by the tripod motion system, with the predetermined set position including three set positions for three linear actuators of the tripod motion system. The method further comprises the tripod motion system moving a positioning actuator of a linear actuator substantially to the corresponding predetermined set position. Each linear actuator of the three linear actuators is coupled to a bottom single-degree-of-freedom (SDOF) hinge on a bottom plate of the tripod motion system and is further coupled to a top three-degrees-of-freedom (TDOF) joint on a top plate of the tripod motion system. The method further comprises the tripod motion system moving one or more displacing actuators of the linear actuator to boost the linear actuator and to hold the linear actuator at the predetermined set position, with the one or more displacing actuators of the linear actuator providing a majority of a displacement force generated by the linear actuator. The method further comprises the tripod motion system rotating a rotator component affixed to the top plate. The rotator component is adapted to receive and rotate a workpiece about a Z-axis of the tripod motion system. The method further comprises the tripod motion system translating a positioning table along one or both of an X-axis and a Y-axis. The bottom plate is affixed to and moved by the positioning table.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A tripod motion system comprising:
a bottom plate including three hinges;
a top plate including three joints, wherein the top plate is configured to receive a workpiece; and
three linear actuators, wherein each linear actuator of the three linear actuators is coupled to an associated one of the three hinges of the bottom plate and coupled to an associated one of the three joints of the top plate;
wherein each linear actuator of the three linear actuators comprises:
a ball coupled to the associated one of the three joints; and
a positioning actuator, configured to, in response to the top plate being displaced by an external force, provide an extension force to return the top plate to a predetermined set position with sub-micron positioning accuracy and move the ball to a predetermined extension position; and
wherein at least one linear actuator of the three linear actuators further comprises one or more displacing actuators configured to provide an actuation force that adds to the extension force to hold the at least one linear actuator at the predetermined set position, wherein the actuation force is a majority of a displacement force generated by the at least one linear actuator.

2. The tripod motion system of claim 1 further comprising a rotator component affixed to at least one of the top plate and the bottom plate, wherein the rotator component is configured to rotate about a Z-axis of the tripod motion system.

3. The tripod motion system of claim 2, wherein the three linear actuators and the rotator component are configured to provide four degrees of freedom of movement.

4. The tripod motion system of claim 3, further comprising a positioning table affixed to at least one of the bottom plate and the top plate, wherein the positioning table is configured to move linearly with respect to an X-axis and move linearly with respect to a Y-axis, and wherein the three linear actuators, the rotator component, and the positioning table are configured to provide six degrees of freedom of movement.

5. The tripod motion system of claim 1, wherein at least one linear actuator of the three linear actuators comprises a positional feedback device that is configured to provide a positional signal to a positioning controller, and wherein the positioning controller is configured to provide a control signal that operates the at least one linear actuator to position the top plate to the predetermined set position.

6. The tripod motion system of claim 5, wherein the at least one linear actuator includes encoder grating that the positional feedback device interacts with to generate the positional signal.

7. The tripod motion system of claim 1, wherein at least one linear actuator of the three linear actuators comprises: the positioning actuator being an electric positioning actuator configured to extend or retract the at least one linear actuator to the predetermined set position; and one or more pneumatic displacing actuators configured to boost the electric positioning actuator and hold the at least one linear actuator at the predetermined set position, wherein the one or more displacing actuators of the at least one linear actuator is configured to provide a majority of a displacement force generated by the at least one linear actuator.

8. The tripod motion system of claim 7, further comprising a pressure regulator that supplies a substantially fixed pneumatic pressure to the one or more displacing actuators.

9. The tripod motion system of claim 1, wherein each linear actuator of the three linear actuators is configured to position the top plate to a new predetermined set position.

10. A tripod motion system comprising:
a bottom plate including three hinges;
a top plate including three joints, wherein the top plate is configured to receive a workpiece;
a plurality of linear actuators, wherein each linear actuator is coupled to an associated one of the three hinges of the bottom plate and coupled to an associated one of the three joints of the top plate; and
a rotator component configured to rotate the top plate by rotating about a Z-axis of the tripod motion system, wherein the plurality of linear actuators and the rotator components are configured to, in response to being displaced by an external force, return the top plate to a predetermined set position with sub-micron positioning accuracy;
wherein at least one linear actuator of the plurality of linear actuators comprises:
a positioning actuator, configured to, in response to the top plate being displaced by the external force, provide an extension force to return the top plate to the predetermined set position with sub-micron positioning accuracy; and one or more displacing actuators configured to provide an actuation force that adds to the extension force to hold the at least one linear actuator at the predetermined set position, wherein the actuation force is a majority of a displacement force generated by the at least one linear actuator.

11. The tripod motion system of claim 10, wherein the plurality of linear actuators consists of three linear actuators.

12. The tripod motion system of claim 10 further comprising a positioning table, wherein the plurality of linear actuators, the positioning table, and the rotator component are configured to provide the tripod motion system with six degrees of freedom of movement.

13. The tripod motion system of claim 10, wherein at least one linear actuator of the plurality of linear actuators comprises a positional feedback device configured to provide a positional signal to a positioning controller, and wherein the positioning controller is configured to provide a control signal that operates the at least one linear actuator to position the top plate to a set position with the sub-micron positioning accuracy.

14. The tripod motion system of claim 13, wherein the at least one linear actuator includes encoder grating that the positional feedback device interacts with to generate the positional signal.

15. The tripod motion system of claim 10, wherein the at least one linear actuator of the plurality of linear actuators comprises:

the positioning actuator being an electric positioning actuator configured to extend or retract the at least one linear actuator to the predetermined set position; and one or more pneumatic displacing actuators configured to boost the electric positioning actuator and hold the at least one linear actuator at the predetermined set position.

16. A method of operating a tripod motion system with six degrees of freedom, the method comprising:

in the tripod motion system, changing a length of at least one linear actuator of three linear actuators over a linear actuation span, wherein each linear actuator of the three linear actuators is coupled to an associated one of three hinges of a bottom plate and coupled to an associated one of three joints of a top plate, wherein the top plate is configured to receive a workpiece; and in the tripod motion system, in response to the top plate being displaced by an external force, returning the top plate to a predetermined set position with sub-micron positioning accuracy by providing an extension force and moving a ball coupled to an associated one of the three joints to a predetermined extension position;

wherein each linear actuator of the three linear actuators comprises:

a positioning actuator, configured to, in response to the top plate being displaced by the external force, provide the extension force to return the top plate to the predetermined set position with sub-micron positioning accuracy and move the ball to the predetermined extension position; and one or more displacing actuators configured to provide an actuation force that adds to the extension force to hold the at least one linear actuator at the predetermined set position, wherein the actuation force is a majority of a displacement force generated by the at least one linear actuator.

17. The method of claim 16, further comprising rotating a rotator component about a z-axis of the tripod motion system, wherein the rotator component is affixed to at least one of the top plate and the bottom plate.

18. The method of claim 17, wherein the three linear actuators and the rotator component provide four degrees of freedom of movement.

* * * * *